United States Patent
Stern et al.

(10) Patent No.: US 10,194,656 B2
(45) Date of Patent: *Feb. 5, 2019

(54) ANIMAL FEED PRESERVATIVE, SUPPLEMENT AND METHODS

(71) Applicant: Hawkins, Inc., Minneapolis, MN (US)

(72) Inventors: Theodore R. Stern, Minneapolis, MN (US); Stephen G. Campano, Glen Allen, VA (US); Gary Carl Larson, Shoreview, MN (US)

(73) Assignee: Hawkins, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/599,561

(22) Filed: May 19, 2017

(65) Prior Publication Data
US 2017/0258084 A1 Sep. 14, 2017

Related U.S. Application Data

(63) Continuation of application No. 14/843,397, filed on Sep. 2, 2015, now Pat. No. 9,675,067.

(60) Provisional application No. 62/045,416, filed on Sep. 3, 2014.

(51) Int. Cl.
*A01N 37/00* (2006.01)
*A01N 37/42* (2006.01)

(52) U.S. Cl.
CPC ................... *A01N 37/42* (2013.01)

(58) Field of Classification Search
CPC ............. A01N 37/42; A23K 1/17; A23K 3/00
USPC ....................................................... 514/557
See application file for complete search history.

(56) References Cited

U.S. PATENT DOCUMENTS

| | | | |
|---|---|---|---|
| 2,831,769 A | 4/1958 | Kamlet | |
| 2,907,658 A | 10/1959 | Luther | |
| 4,220,661 A | 9/1980 | Huitson | |
| 6,183,794 B1 | 2/2001 | Kaesler et al. | |
| 7,816,514 B2 | 10/2010 | Fosdick et al. | |
| 8,034,925 B2 | 10/2011 | Fosdick et al. | |
| 9,675,067 B2 * | 6/2017 | Stern ................ | A01N 37/42 |
| 2003/0147930 A1 | 8/2003 | Jun et al. | |
| 2005/0244555 A1 | 11/2005 | Ghorpade et al. | |
| 2006/0172392 A1 | 8/2006 | Zhou et al. | |
| 2006/0178344 A1 | 8/2006 | Anderson et al. | |
| 2008/0045592 A1 | 2/2008 | Broadbent et al. | |
| 2010/0222566 A1 | 9/2010 | Fosdick et al. | |
| 2010/0312006 A1 | 12/2010 | Lake et al. | |
| 2012/0136051 A1 | 5/2012 | Li et al. | |
| 2012/0148716 A1 | 6/2012 | Doyle et al. | |
| 2016/0058038 A1 | 3/2016 | Stern et al. | |

FOREIGN PATENT DOCUMENTS

| | | |
|---|---|---|
| GB | 1252538 | 11/1971 |
| WO | 2016036932 | 3/2016 |

OTHER PUBLICATIONS

File History for U.S. Appl. No. 14/843,397, (241 pages).
"International Preliminary Report on Patentability," for PCT/US2015/048294 dated Mar. 16, 2017 (8 pages).
"International Search Report & Written Opinion," for PCT/US2015/048294 dated Nov. 30, 2015 (12 pages).
Weiss, Bill et al., "Hay Preservatives," Ohio State University Extension, Dept. of Horticulture and Crop Science, date unknown (4 pages).

* cited by examiner

*Primary Examiner* — Taylor V Oh
(74) *Attorney, Agent, or Firm* — Pauly, DeVries Smith & Deffner LLC

(57) ABSTRACT

Embodiments herein relate to animal feed preservatives including byproducts containing levulinic acid and methods of making and using the same. In an embodiment, a method of making an animal feed preservative is included. The method can include obtaining an acidic byproduct of a manufacturing process. The acidic byproduct can include at least about 1% by weight levulinic acid or a salt thereof. The method can further include mixing the acidic byproduct with a base to form the animal feed preservative. The animal feed preservative can include at least about 5 wt. % of the acid byproduct. In various embodiments, a method of reducing the amount of mycotoxins formed in an animal feed product during storage is included. In various embodiments, an animal feed preservative or supplement is included. Other embodiments are also included herein.

18 Claims, No Drawings

ANIMAL FEED PRESERVATIVE, SUPPLEMENT AND METHODS

This application is a continuation application of U.S. application Ser. No. 14/843,397, filed Sep. 2, 2015, which claims the benefit of U.S. Provisional Application No. 62/045,416, filed Sep. 3, 2014, the contents of all of which are herein incorporated by reference in their entireties.

FIELD

Embodiments herein relate to animal feed preservatives, supplements and methods of making or using the same. More specifically, embodiments herein relate to animal feed preservatives and supplements including byproducts containing levulinic acid and methods of making and using the same.

BACKGROUND

Mold growth in food materials, and particularly in animal feeds, is a problem when such materials are stored, such as in the case of hay, grain, and other forage materials. Molds are a type of fungi and are almost ubiquitous in small quantities due to the large number of their small spores in the environment. Common molds can include *Acremonium, Alternaria, Aspergillus, Cladosporium, Fusarium, Mucor, Penicillium, Rhizopus, Stachybotrys* and *Trichoderma*. Molds consume organic matter wherein humidity and temperatures are sufficient.

One reason molds present a problem is that some can produce dangerous mycotoxins. Mycotoxins are poisonous by-products produced by molds as they grow. Mycotoxins are known to be damaging to livestock when present in hay and other animal feed. For example, one of the common molds, *Aspergillus flavus*, produces the mycotoxin aflatoxin which, in addition to other toxic characteristics, interferes with the immune system's ability to produce gamma globulin, the protein that is part of the immune system. The resulting breakdown of the immune system then renders animals that have ingested such mold vulnerable to a variety of diseases.

SUMMARY

Embodiments herein relate to animal feed preservatives and supplements including byproducts containing levulinic acid and methods of making and using the same. In an embodiment, a method of making an animal feed preservative or supplement is included. The method can include obtaining an acidic byproduct of a manufacturing process. The acidic byproduct can include at least about 1% by weight levulinic acid or a salt thereof. The method can further include mixing the acidic byproduct with a base to form the animal feed preservative. The animal feed preservative can include at least about 5 wt. % of the acid byproduct.

In various embodiments, a method of reducing the amount of mycotoxins formed in an animal feed product during storage is included. The method can further include applying an effective amount of an animal feed preservative to the animal feed product. The animal feed preservative can include at least about 20% by weight of an acidic byproduct of a manufacturing process. The acidic byproduct can include at least about 10% by weight of levulinic acid or a salt thereof and at least about 10% by weight of hydrochloric acid. The animal feed preservative can also include at least about 0.5% by weight of acetic acid or a salt thereof.

In various embodiments, an animal feed preservative is included herein. The animal feed preservative can include at least about 60% by weight of propionic acid or a salt thereof. The animal feed preservative can also include at least about 20% by weight of an acidic byproduct of a manufacturing process, the acidic byproduct comprising at least about 10% by weight of levulinic acid or a salt thereof and at least about 10% by weight of hydrochloric acid. The animal feed preservative can also include at least about 0.5% by weight of acetic acid or a salt thereof.

In various embodiments, an animal feed supplement is included herein. The animal feed supplement can include at least about 60% by weight of propionic acid or a salt thereof. The animal feed supplement can also include at least about 20% by weight of an acidic byproduct of a manufacturing process, the acidic byproduct comprising at least about 10% by weight of levulinic acid or a salt thereof and at least about 10% by weight of hydrochloric acid. The animal feed supplement can also include at least about 0.5% by weight of acetic acid or a salt thereof.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

DETAILED DESCRIPTION

The embodiments described herein are not intended to be exhaustive or to limit to the precise forms disclosed in the following detailed description. Rather, the embodiments are chosen and described so that others skilled in the art can appreciate and understand the principles and practices of embodiments herein.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Applicants have discovered that certain byproducts of manufacturing processes, such as those including levulinic acid or salts thereof, are surprisingly effective as animal feed preservatives. Specifically, as demonstrated in examples 1 and 2 below, the animal feed preservative compositions herein containing a byproduct with levulinic acid show a remarkable and surprising degree of efficacy compared to other compositions for the inhibition of mold growth as tested on actual samples of animal forage.

In various embodiments, an animal feed preservative composition is included. The animal feed preservative composition can include an acidic byproduct of a manufacturing process. In some embodiments, the acidic byproduct is a byproduct of a carboxylic acid manufacturing process. In some embodiments, the acidic byproduct is a byproduct of a glucosamine manufacturing process. In some embodiments, the acidic byproduct is a byproduct of a different manufacturing process. The composition can be used to inhibit the growth of microorganisms in animal forage feeds.

By way of example, the composition can be used to inhibit the growth of mold in animal forage feeds.

In various embodiments, a method for preserving animal forage feeds is included herein. The method can include applying a composition comprising an acidic byproduct of a manufacturing process to an animal feed product. The acid byproduct can include acids including, but not limited to, levulinic acid and other organic acids.

In various embodiments, an animal feed preservative composition is included. The animal feed preservative composition can include an acidic byproduct of a manufacturing process. In some embodiments, the acidic byproduct is a byproduct of a carboxylic acid manufacturing process. In some embodiments, the acidic byproduct is a byproduct of a glucosamine manufacturing process. In some embodiments, the acidic byproduct is a byproduct of a different manufacturing process.

It will be appreciated that the category of animal feeds can include plant material from many different species of plants. Animal forage feeds can specifically include, but are not limited to, grasses, hay, alfalfa, grains, immature cereal crops, herbaceous legumes, tree legumes, crop residue, and the like. As such, embodiments herein can include compositions for preserving one or more of the preceding forage feeds. Embodiments herein can also include methods for preserving one or more of the preceding forage feeds.

As stated above, in various embodiments, compositions herein can include an acidic byproduct. The acidic byproduct can be a liquid comprising a mixture of organic acids and other products. As an example, levulinic acid (also known as acetyl-propionic acid), is present in particular embodiments of the disclosed mixtures. In some embodiments, a composition containing a substantially similar mixture of components to the byproduct can be used instead of the byproduct, or in partial replacement of the byproduct.

In some embodiments, the amount of the acidic byproduct in the preservative or supplement composition overall can be at least about 0.5 wt. %, or at least about 1.0 wt. %, or at least about 2.0 wt. %, or at least about 3.0 wt. %, or at least about 4.0 wt. %, or at least about 5.0 wt. %, or at least about 7.5 wt. %, or at least about 10.0 wt. %, or at least about 15.0 wt. %, or at least about 20.0 wt. %, or at least about 25.0 wt. %, or at least about 30.0 wt. %, or at least about 35.0 wt. %, or at least about 40.0 wt. %, or at least about 45.0 wt. %, or at least about 50.0 wt. %, or at least about 55.0 wt. %, or at least about 60.0 wt. %, or at least about 65.0 wt. %, or at least about 70.0 wt. %, or at least about 75.0 wt. %. In various embodiments, the amount of the acidic byproduct in the preservative or supplement composition overall can be within a range wherein the upper and lower bounds of the range can be any of the preceding numbers provided that the upper bound is higher than the lower bound.

It will be appreciated that acidic byproducts used herein can be formed as a result of many different chemical production processes. In an embodiment, the acidic byproduct is produced as a byproduct of a reaction to produce glucosamine products from chitin derived from various types of fungal biomass. Such reaction processes are disclosed in U.S. Pat. No. 8,034,925 and U.S. Pat. No. 7,816,514 which are herein incorporated by reference. Chitin is a natural polysaccharide, with the structure of an unbranched polymer of 2-acetoamido-2-deoxy-D-glucose (N-acetyl-D-glucosamine). The formula for chitin can be represented by the general repeating structure:

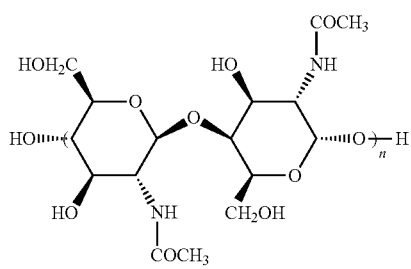 [SMILES: CC(=O)N[C@H]1[C@H](O[C@H]2[C@@H](O)[C@H](NC(C)=O)[C@H](O)O[C@H]2CO)O[C@H](CO)[C@@H](O)[C@@H]1O]

In various glucosamine production processes, the polymeric structure of the chitin is transformed into individual units of glucosamine, which is also known as 2-amino-2-deoxy-D-glucose. Structurally, glucosamine is modified glucose with an amine group replacing the OH group found on the carbon two (C-2) atom. The general structure of glucosamine is:

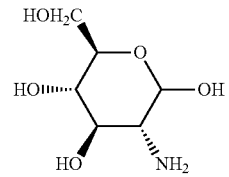

Although glucosamine is a primary product obtained from the chitin reaction, other species are also frequently produced, including an acidic byproduct stream comprising a mixture comprising mixed acids that can be used in accordance with various embodiments herein. This byproduct stream can contain glucan conversion materials, such as melanoidins and levulinic acids. In addition, other species such as dextrose, glucose, unreacted chitin, and salts can remain after the glucosamine has been produced and separated.

It will be appreciated, that glucosamine separation frequently results in a residual amount of glucosamine in the acidic byproduct stream. As such, in various embodiments, the acidic byproduct can include an amount of glucosamine (such as in the form of glucosamine HCl) of at least about 0.5 wt. %, or at least about 1.0 wt. %, or at least about 2.0 wt. %, or at least about 4.0 wt. %. In some embodiments, the byproduct stream can include an amount of glucosamine (such as in the form of glucosamine HCl) of about 2 wt. % to about 5 wt. %.

The acidic byproduct may also include polymerized Maillard reagents, also known as melanoidins. Melanoidins are relatively complex, high molecular weight, irregular polymers and are present in particular embodiments of the mixtures. Without being tied to any particular theory, melanoidins are likely formed by the conversion of glucans to dextrose to hydroxymethylurfural (HMF) to produce melanoidins in a glucosamine production process. (The reaction may produce other glucan-derived products and amines from proteins in a biomass source as well as lipids in such a source.) Such a chemical process is known as the Maillard Reaction.

One example of the components within an exemplary acidic byproduct, and exemplary ranges for the same, is shown in Table 1.

TABLE 1

Content and Properties of Acidic Byproduct

| Item | Range |
| --- | --- |
| % Cl⁻ as HCl, w/w % | 10-15% |
| % Total Acid as HCl, w/w % | 20-25% |
| % Levulinic Acid, w/w % | 15-25% |
| % Organic Acids, w/w % | 3-14% |

An example of the organic acid content (other than levulinic acid) and exemplary ranges for the same, is shown in Table 2.

TABLE 2

Organic Acid Content of Acidic Byproduct

| Item | Range |
| --- | --- |
| % Citric Acid, w/w % | 1-5% |
| % Formic Acid, w/w % | 0.5-3% |
| % Acetic Acid, w/w % | 0.5-3% |

Other production processes that can result in acidic byproducts useful in conjunction with embodiments herein can include biomass reforming processes such as processes for converting paper mill sludge, municipal solid waste, waste paper, waste wood, agricultural residues, and the like. In various such processes, cellulose can be converted to a sugar, which can then be converted into levulinic acid. Other production processes that can result in acidic byproducts useful in conjunction with embodiments herein can include production processes for citric acid and ethanol. In some embodiments, the acidic byproduct can be a direct byproduct of a production process. In other embodiments, the acidic byproduct can be an indirect byproduct of a production process, such as in the case of a direct byproduct being further processed in order to generate an acidic byproduct such those described herein.

It will be appreciated that the weight percentage of the acids and other ingredients in the acidic byproduct can vary due to changes in the manufacturing materials and processes. However, in some embodiments, the acidic byproduct includes at least about 1% levulinic acid by weight. In an embodiment, the acidic byproduct includes at least about 5% levulinic acid by weight. In an embodiment, the acidic byproduct includes at least about 10% levulinic acid by weight. In another embodiment, the acidic byproduct includes at least about 15% levulinic acid by weight. In another embodiment, the acidic byproduct includes at least about 20% levulinic acid by weight. In various embodiments, the amount of levulinic acid in the acidic byproduct falls in a range wherein any of the preceding amounts can be the lower or upper bound of the range, provide the upper bound is greater than the lower bound.

In some embodiments, the acidic byproduct can include at least about 1% hydrochloric acid by weight. In some embodiments, the acidic byproduct can include at least about 5% hydrochloric acid by weight. In some embodiments, the acidic byproduct can include at least about 10% hydrochloric acid by weight. In other embodiments, the acidic byproduct can include at least 15% hydrochloric acid by weight. In various embodiments, the amount of hydrochloric acid in the acidic byproduct falls in a range wherein any of the preceding amounts can be the lower or upper bound of the range, provide the upper bound is greater than the lower bound.

In embodiments, the acidic byproduct includes at least about 1% chloride ion content by weight. In embodiments, the acidic byproduct includes at least about 5% chloride ion content by weight. In embodiments, the acidic byproduct includes at least about 10% chloride ion content by weight. In embodiments, the acidic byproduct includes at least about 15% chloride ion content by weight. In embodiments, the acidic byproduct includes at least about 20% chloride ion content by weight. In various embodiments, the amount of chloride ion in the acidic byproduct falls in a range wherein any of the preceding amounts can be the lower or upper bound of the range, provided the upper bound is greater than the lower bound.

In embodiment, the acidic byproduct further includes polymerized Maillard reaction agents, or melanoidins (high molecular weight heterogeneous polymers that are formed when sugars and amino acids combine at high temperatures and low water activity). In some embodiments, the acid byproduct can include at least about 0.1% melanoidins by weight. In some embodiments, the acid byproduct can include at least about 0.5% melanoidins by weight. In some embodiments, the acid byproduct can include at least about 1.0% melanoidins by weight. In some embodiments, the acid byproduct can include at least about 2.0% melanoidins by weight.

In addition to the acidic byproduct, the antimicrobial preservative or supplement composition can also include other components, such as a base and/or a carboxylic acid species. By way of example, in some embodiments, the acidic byproduct can be mixed with a carboxylic acid and/or a base to make an animal feed preservative.

Various bases can be added to the preservative or supplement composition. In some embodiments, the base can include a hydroxide salt. Exemplary hydroxide salts can include, but are not limited to, metal hydroxide salts, such as alkali metal hydroxide salts and alkaline earth metal hydroxide salts. Exemplary metal hydroxide salts can include, but are not limited to, sodium hydroxide, potassium hydroxide, calcium hydroxide, magnesium hydroxide, and the like.

In some embodiments, the base can include ammonia. In some embodiments, a base with an ammonium group can be used. Exemplary bases including ammonium groups can include, but are not limited to, ammonium hydroxide.

The amount of the base added can be an effective amount to adjust the pH of the composition (including the acidic byproduct as well as the other components of the composition) to be between about 4.0 and about 8.0, or between about 5.0 and about 7.0. In various embodiments, the pH of the animal feed preservative or supplement can be adjusted to meet the application requirements where it is used. In some embodiments, buffers or other solutions can be added to the preservative or supplement to maintain its pH within a targeted range.

In various embodiments, one or more acids can be added to the composition in addition to the acidic byproduct. Those of skill in the art will appreciate that inclusion of a salt of an acid (including but not limited to ammonium and metal salts thereof), as opposed to the acid itself can provide benefits in terms of ease of formulation. However, either the acid or the salt of the acid can be used. In some embodiments, the acid can be a weak acid. In some embodiments, the acid can be a carboxylic acid.

In some embodiments, the amount of the one or more carboxylic acid species in the preservative or supplement composition can be at least about 0.5 wt. %, or at least about 1.0 wt. %, or at least about 2.0 wt. %, or at least about 3.0 wt. %, or at least about 4.0 wt. %, or at least about 5.0 wt.

%, or at least about 7.5 wt. %, or at least about 10.0 wt. %, or at least about 15.0 wt. %, or at least about 20.0 wt. %, or at least about 30.0 wt. %, or at least about 40.0 wt. %, or at least about 50.0 wt. %, or at least about 60.0 wt. %, or at least about 70.0 wt. %.

In some embodiments, the carboxylic acid species can include acetic acid or a salt of acetic acid. In some embodiments, the carboxylic acid species can include propionic acid or a salt thereof.

In some embodiments, the animal feed preservative can specifically be a forage preservative. In some embodiments the animal feed preservative can be a hay preservative.

It will be appreciated that the animal feed preservative or supplement can include other acid components or their conjugate bases. As an example, the animal feed preservative can include sorbic acid, lactic acid, succinic acid, tartaric acid, benzoic acid, citric acid, malic acid, their conjugate bases, or combinations thereof.

In some embodiments, the animal feed preservative or supplement can include, in some cases, at least about 1% by weight of ammonium acetate or a reaction product thereof. In some embodiments, the animal feed preservative or supplement can include, in some cases, at least about 2% by weight of ammonium acetate or a reaction product thereof. In some embodiments, the animal feed preservative or supplement can include, in some cases, at least about 3% by weight of ammonium acetate or a reaction product thereof. In some embodiments, the animal feed preservative or supplement can include, in some cases, at least about 4% by weight of ammonium acetate or a reaction product thereof. In some embodiments, the animal feed preservative or supplement can include, in some cases, at least about 5% by weight of ammonium acetate or a reaction product thereof.

In some embodiments, the animal feed preservative or supplement can also include a surfactant.

In some embodiments, preservative or supplement compositions herein can be formulated as a liquid in an aqueous solvent. In other embodiments, preservative compositions or supplement herein can be formulated as a dry mixture. In some embodiments, all components of the preservative composition or supplement are substantially dissolved in the aqueous solvent. In some embodiments, the preservative composition or supplement is a liquid with a total solids content of between about 0.5% and about 70% by weight, or about 0.5% and about 60% by weight, or about 0.5% and about 40% by weight, or about 0.5% and about 20% by weight, or about 0.5% and about 10% by weight, or about 0.5% and about 3% by weight, or between about 1% and 2% by weight.

In use, the liquid composition can be applied by spraying, dipping, injection, brushing or the like. The liquid composition can be thoroughly mixed into the forage or other animal food material. In some embodiments, the liquid composition can be diluted before application. For example, the liquid composition can be diluted in water to various concentrations. In some embodiments, the liquid composition can be diluted in water at a ratio (preservative:water) of about 1:0.5, or about 1:0.75, or about 1:1, or about 1:1.5, or about 1:2, or about 1:2.5, or about 1:3, or about 1:4, or about 1:5, or about 1:6.

Embodiments herein can include a method of reducing the amount of mycotoxins formed in an animal feed product during storage comprising applying an effective amount of an animal feed preservative to an animal feed product. In various embodiments, the animal feed preservative can include at least about 20% by weight of an acidic byproduct of a manufacturing process. The acidic byproduct can include at least about 10% by weight of levulinic acid or a salt thereof and at least about 10% by weight of hydrochloric acid. In various embodiments, the animal feed preservative can include at least about 0.5% by weight of acetic acid or a salt thereof.

It will be appreciated that references herein to the use of acids can also include the use of salts of such acids, unless the specific context dictates otherwise. Common cations in such salts can include metals ions, including but not limited to sodium, potassium, calcium, and the like, as well as ammonium.

It will be appreciated that various other steps can also be taken in conjunction with methods herein. By way of example, components of the composition (individually or after being mixed together) can be filtered, centrifuged, heated, cooled, concentrated, diluted, or the like.

Aspects herein may be better understood with reference to the following examples. These examples are intended to be representative of specific embodiments, and are not intended as limiting of the scope herein.

EXAMPLES

Example 1: Mold Inhibition on Alfalfa Hay

Samples of preservatives were prepared and tested for their performance as mold inhibitors. The sample compositions were compared to a hay preservative product that is 100% ammonium propionate ("AM-PROP-100"). Formulations were prepared by mixing the AM-PROP-100 preservative with different percentages of ammonium acetate solution and the acidic byproduct solution. The composition of the mixed organic acid stream is given in Table 1 above. To prepare the ammonium acetate solution, ammonium acetate was diluted to 80% with water and neutralized to pH 6.00 with ammonium hydroxide. Table 2 gives the percentages of each solution in the compositions.

TABLE 2

| Formulation Sample No. | Ammonium Propionate (std formula) | Ammonium acetate | Acidic Byproduct |
| --- | --- | --- | --- |
| Formulation E1 | 65% | 5% | 30% |
| Formulation E2 | 75% | 0% | 25% |
| AM-PROP-100 | 100% | 0% | 0% |

Compositions were tested on alfalfa hay baled at a moisture content of 14% and under, and barn-stored for approximately 7 months. For the testing, four 4.8 lb. samples were re-wetted to 21-24% moisture. Three of the samples were treated with the three formulations listed above using a treatment level of 0.8% (w/w), which corresponds to the 16 lb/ton equivalent recommended for Baled Hay Additives at moisture levels of 26-30%). The three treated samples and a control sample were then placed into a common chamber housing and stored for 1 week at 21-24% moisture by introducing warm steam into the chamber. After 1 week, the samples were analyzed for visible mold and mold counts were taken by Dairyland Labs, Arcadia, Wis. Results of the analysis are shown in Table 3

TABLE 3

| Formulation Sample No. | Total Mold Count (cfu/gram) | Total Yeast count (cfu/gram) |
|---|---|---|
| Formulation E1 | 22,000 | <1,000 |
| Formulation E2 | 500,000 | 100,000 |
| AM-PROP-100 | 800,000 | 1,200,000 |
| CONTROL | 2,000,000 | 1,300,000 |

Example 2: Microorganism Growth Inhibition on Agar Plates

The three compositions from Example 1 were also tested for their mold inhibitor performance by measuring the in-situ growth inhibition of different organisms using zone of inhibition assays with agar plates. Formulations were tested against strains of the following: *Aspergillus flavus, Fusarium oxysporum, Penicillium chrysogenum, Mucor circinelloides* (all fungi); *Candida albicans* (yeast); and *Escherichia coli* and *Salmonella choleraesuis* (bacteria).

Inoculum of test organisms of about $10^8$ cells/ml prepared prior to testing were streaked on Sabouraud Dextrose Agar, Emmons (*A. flavus, F. oxysporum, P. chrysogenum, M. circinelloides* and *C. albicans*) or Tryptic Soy Agar (*E. coli* and *S. choleraesuis*) using a sterile small cotton tipped swab (Fisherbrand, Waltham, Mass.). To achieve uniform growth, the swab was in streaked in one direction, then followed by rotating the plate 90° and streak the plate in that direction. This step was carried out 3 times and plates were allowed to dry to at least 5 minutes.

Sterile paper filter disks approximately 7 mm in size were impregnated with the mold inhibitor formulations by spotting 15 ul onto the filter disks and allowing the solution to be absorbed for 30 minutes inside a laminar flow hood. Using sterile forceps, three (3) filter disks saturated by mold inhibitor were aseptically transferred on the surface of inoculated plates, allowed to dry for 15 minutes prior to incubation at 28° C. Plates were examined at 48 and 96 hours to monitor signs of in situ growth inhibition, measured as diameter with a Vernier caliper.

The zone of inhibition testing showed that all three formulations exhibited consistently robust inhibition against all the mold, yeast, and bacteria strains tested.

Comparing the results of Example 1 with Example 2, it can be seen that while many compositions show at least some efficacy against a variety of microorganisms as tested on agar plates, the compositions herein containing a byproduct with levulinic acid show a remarkable and surprising degree of efficacy compared to other compositions for the inhibition of mold growth as tested on actual samples of animal forage.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this disclosure pertains. All publications and patent applications are herein incorporated by reference to the same extent as if each individual publication or patent application was specifically and individually indicated by reference.

Aspects herein have been described with reference to various specific and preferred embodiments and techniques. However, it should be understood that many variations and modifications may be made while remaining within the spirit and scope herein.

The invention claimed is:

1. An animal feed preservative comprising:
   10% to 75% by weight of propionic acid or a salt thereof;
   at least 10% by weight of an acidic byproduct of a manufacturing process, the acidic byproduct comprising at least 5% by weight of levulinic acid or a salt thereof and at least 5% by weight of hydrochloric acid;
   at least 0.5% by weight of at least one carboxylic acid or a salt thereof; and
   wherein the pH of the animal feed preservative is from 4.0 to 8.0.

2. The animal feed preservative of claim 1, the at least one carboxylic acid or a salt thereof comprising acetic acid or salt thereof.

3. The animal feed preservative of claim 2, further comprising at least 5 wt. % acetic acid or a salt thereof.

4. The animal feed preservative of claim 1, the acidic byproduct further comprising at least 10 wt. % levulinic acid.

5. The animal feed preservative of claim 1, the acidic byproduct further comprising at least 10 wt. % hydrochloric acid.

6. The animal feed preservative of claim 1, wherein the pH of the animal feed preservative is from 5.0 to 7.0.

7. The animal feed preservative of claim 1, further comprising at least one of sorbic acid, lactic acid, succinic acid, tartaric acid, benzoic acid, citric acid, malic acid, their conjugate bases, or combinations thereof.

8. The animal feed preservative of claim 1, further comprising at least 1 wt. % polymerized Maillard reaction products.

9. The animal feed preservative of claim 1, the acidic byproduct being a byproduct of a glucosamine manufacturing process, the acidic byproduct further comprising a residual amount of glucosamine from 0.5 wt. % to 5 wt. %.

10. The animal feed preservative of claim 1, further comprising melanoidins.

11. An animal feed supplement comprising:
    10% to 75% by weight of propionic acid or a salt thereof;
    at least 10% by weight of an acidic byproduct of a manufacturing process, the acidic byproduct at least 5% by weight of hydrochloric acid; and
    at least 0.5% by weight of acetic acid or a salt thereof.

12. The animal feed supplement of claim 11, comprising at least 5 wt. % acetic acid or a salt thereof.

13. The animal feed supplement of claim 11, the acidic byproduct further comprising at least 10 wt. % levulinic acid or a salt thereof.

14. The animal feed supplement of claim 11, the acidic byproduct further comprising at least 10 wt. % hydrochloric acid.

15. The animal feed supplement of claim 11, further comprising at least one of sorbic acid, lactic acid, succinic acid, tartaric acid, benzoic acid, citric acid, malic acid, their conjugate bases, or combinations thereof.

16. The animal feed supplement of claim 11, further comprising at least 1 wt. % polymerized Maillard reaction products.

17. The animal feed preservative of claim 1, further comprising at least 25 wt. % acidic byproduct of a manufacturing process.

18. The animal feed supplement of claim 11, further comprising at least 25 wt. % acidic byproduct of a manufacturing process.

* * * * *